United States Patent
Schnider et al.

(10) Patent No.: US 10,265,327 B2
(45) Date of Patent: Apr. 23, 2019

(54) V1A ANTAGONISTS TO TREAT PHASE SHIFT SLEEP DISORDERS (71) Applicant: Hoffmann-La Roche Inc., Little Falls, NJ (US)

(72) Inventors: Patrick Schnider, Bottmingen (CH); Christophe Grundschober, Rodersdorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/065,574

(22) Filed: Mar. 9, 2016

(65) Prior Publication Data
US 2018/0064727 A1 Mar. 8, 2018

Related U.S. Application Data (63) Continuation of application No. PCT/EP2014/067264, filed on Aug. 12, 2014.

(30) Foreign Application Priority Data

Aug. 19, 2013 (EP) .................... 13180836

(51) Int. Cl.
*C07D 487/04* (2006.01)
*A61K 31/5517* (2006.01)

(52) U.S. Cl.
CPC ............... *A61K 31/5517* (2013.01)

(58) Field of Classification Search
CPC ............ C07D 487/04; A61K 31/5517
See application file for complete search history.

(56) References Cited

FOREIGN PATENT DOCUMENTS

| WO | 02/055514 A2 | 7/2002 |
|---|---|---|
| WO | 03/051356 A1 | 6/2003 |
| WO | 2004/074291 A1 | 9/2004 |
| WO | 2006/021882 A1 | 3/2006 |
| WO | 2010/060836 A1 | 6/2010 |
| WO | 2013/176220 A1 | 11/2013 |

OTHER PUBLICATIONS

Helen M. Murphy et al., "The Role of Vasopressin in Modulating Circadian Rhythm Responses to Phase Shifts" Peptides (XP55124590), 19(7):1191-1208 ( 1998).

Jia-Da Li et al., "Vasopressin receptor V1a regulates circadian rhythms of locomotor activity and expression of clock-controlled genes in the suprachiasmatic nuclei" Am J Physiol Regul Integr Comp Physiol 296:R824-R830 ( 2009).

Man Tsuey Tse, "Target identification; Blocking vasopressin receptors reduces jet lag" Nature Reviews Drug Discovery (AOP, published online Nov. 15, 2013; doi:10.1038/nrd4180; (XP55124466), 12 ( 2013).

Written Opinion for PCT/EP2014/067264, (2014).

*Primary Examiner* — Bruck Kifle
(74) *Attorney, Agent, or Firm* — Robert C. Hall (57) ABSTRACT

This invention relates to a new medical use for certain chemical compounds and pharmaceutical compositions containing them. The invention relates to compounds which are selective V1a antagonists for use in the treatment of phase shift sleep disorders, in particular jetlag. In another aspect, the invention relates to a pharmaceutical composition for use in the treatment of phase shift sleep disorders comprising a compound according to the invention and a pharmaceutically acceptable carrier.

11 Claims, 5 Drawing Sheets

V1A ANTAGONISTS TO TREAT PHASE SHIFT SLEEP DISORDERS

CROSS REFERENCE TO RELATED APPLICATIONS

This application is a Continuation of Application No. PCT/EP2014/067264 filed on Aug. 12, 2014, which claims priority to EP Application No. 13180836.2 filed on Aug. 19, 2013, the disclosures of which are incorporated herein by reference in their entirety.

SUMMARY OF THE INVENTION

This invention relates to a new medical use for certain chemical compounds and pharmaceutical compositions containing them. The invention relates to compounds which are V1a antagonists to treat phase shift sleep disorders, in particular jetlag. In another aspect, the invention relates to a pharmaceutical composition for use in the treatment of phase shift sleep disorders comprising a compound according to the invention and a pharmaceutically acceptable carrier.

BACKGROUND OF THE INVENTION

The suprachiasmatic nucleus (SCN) is the endogenous clock of the body regulating circadian rhythmicity and is known to be rich in vasopressin neurons (Kalsbeek et al. 2010)[1], producing and releasing vasopressin with a 24 h circadian rhythm (Schwartz et al. 1983)[2]. A major regulatory effect of vasopressin on circadian rhythm could not be demonstrated by the prior art. The Brattleboro rat, a rat strain naturally lacking vasopressin due to a point mutation, has no obvious defect in its circadian rhythm (Groblewski et al. 1981)[3]. Injection of vasopressin directly in the hamster SCN had no effect on circadian phase shift (Albers et al. 1984)[4]. In contrast, vasopressin may modulate the circadian clock in a more subtle way. Vasopressin deficient Brattleboro rats do not respond to a 6 h phase advance of the light-dark period, but remain synchronized to the food presentation (Murphy et al. 1998)[5], in contrast to normal rats, which respond both to the new light dark rhythm and to food presentation.

More specifically, the vasopressin V1a receptor was shown to have a modulatory role on circadian behavior by studying V1a knock-out (KO) mice. V1a KO mice behave normally under a normal 12 h-12 h light-dark cycle, but in absence of light (dark-dark conditions) these mice show a gradual loss of circadian rhythm characterized by an expansion of the active period. Nevertheless they still respond normally to phase-shifts induced by brief light exposure during the dark phase (Li et al. 2009)[6].

We surprisingly found that administration of a single dose of a small molecule V1a antagonist to normal mice before a 6 h phase shift (6 h advance of light phase) induces a significantly faster re-entrainment to the new light-dark cycle than vehicle treated mice. More specifically, a selective V1a antagonist.

This finding is contrary to the prior art teaching, where treatment with melatonin to accelerate re-entrainment after a phase-shift, is only effective after daily administration for 3 days after the phase advance (Dubocovich et al. 2005)[7].

Poor sleep can lead to numerous health disturbances including anxiety, depression, irritability, impaired social interactions and psychomotor coordination and the like.

WO 2013/176220[8] describes circadian rhythm-regulating agents which comprises an inhibitor capable of inhibiting vasopressin receptors V1a and V1b.

V1a antagonists have been described in the prior art, e.g. in EP 0382185, EP 0526348, WO 94/01113, WO 94/18975, WO 95/06035, WO 96/22292, WO 96/22293, WO 97/49707, WO 97/49708, WO 98/24430, WO 99/37637, WO 99/44613, WO 99/55340, WO 99/65525, WO 00/029405, WO 00/066117, WO 01/058880, WO 01/066109, WO 02/002531, WO 02/044179, WO 02/055514, WO 03/031407, WO 03/037901, WO 03/042181, WO 04/074291, WO 04/108138, WO 2005/039565, WO 2005/063754, WO 2006/020491, WO 2006/021213, WO 2006/051851, WO 2006/058705, WO 2006/102283, WO 2006/102308, WO 2007/006688, WO 2007/009906, WO 2007/014851, WO 2007/039438, WO 2007/077122, WO 2007/109615, WO 2008/068159, WO 2008/068183, WO 2008/068184, WO 2008/068185, WO 2008/077810, WO 2008/077811, WO 2008/080842, WO 2008/080844, WO 2008/084005, WO 2010/057795, WO 2010/060836, WO 2011/120877, WO 2011/128265, WO 2011/131596, WO 2011/134877, WO

BRIEF DESCRIPTION OF THE DRAWINGS

FIG. 1 provides diagrammatic and graphical representations of behavioral phase shifts after administration of V1a antagonist.

FIG. 2 is a graphical representation of the endogenous period of locomotion after administration of V1a antagonist.

FIG. 3 provides diagrammatic and graphical representations of behavioral re-entrainment after administration of V1a antagonist.

FIG. 4 provides diagrammatic and graphical representations of behavioral re-entrainment after administration of V1a antagonist.

DETAILED DESCRIPTION OF THE INVENTION

The following definitions of the general terms used in the present description apply irrespectively of whether the terms in question appear alone or in combination with other groups.

The term "phase shift sleep disorders" summarizes conditions classified as disturbances in the circadian rhythm, i.e. the approximately 24-hour cycles that are generated by an organism, e.g. a human being.

Phase shift sleep disorders include, but are not limited to transient disorders like jetlag or or a changed sleep schedule due to work, social responsibilities, or illness, as well as chronic disorders like delayed sleep-phase syndrome (DSPS), delayed sleep-phase type (DSPT), advanced sleep-phase syndrome (ASPS), and irregular sleep-wake cycle.

The term "V1a antagonist" refers to antagonists of the V1a vasopressin receptor subtype. Examples include OPC-21268, OPC-31260, OPC-41061, VPA-985, SR-49059, SR-121463, VP-343, FR-161282, CI-1025, SRX-251, SRX-246, JNJ-17158063, FE-202158, VT-913, LY307174, Org-52186, PF-184563, YM-218, 1-({(2R,3S)-5-chloro-3-(2-chlorophenyl)-1-[3,4-dimethoxyphenyl)sulfonyl]-3-hydroxy-2,3-dihydro-1H-indol-2-yl}carbonyl)-L-prolinamide, [6-chloro-1-[2-(dimethylamino)ethyl]indol-3-yl]-spiro[1H-isobenzofuran-3,4'-piperidine]-1'-yl-methanone, 8-Chloro-5-methyl-1-(3,4,5,6-tetrahydro-2H-[1,2']bipyridinyl-4-yl)-5,6-dihydro-4H-2,3,5,10b-tetraaza-benzo[e]azulene, trans-8-chloro-5-methyl-1-(4-pyridin-2-yloxycyclohexyl)-4,6-dihydro-[1,2,4]triazolo[4,3-a][1,4]
benzodiazepine and the like. The term "selective V1a antagonist" refers to selectivity of V1a over V1b receptor subtype. An example is trans-8-chloro-5-methyl-1-(4-pyridin-2-yloxycyclohexyl)-4,6-dihydro-[1,2,4]triazolo[4,3-a][1,4]benzodiazepine.

As used herein, the term "alkyl", alone or in combination with other groups, denotes a saturated, i.e. aliphatic, hydrocarbon group including a straight or branched carbon chain. If not further specified, "alkyl" groups denote groups with 1 to 12 carbon atoms, like "$C_{1-12}$-alkyl". "$C_{1-4}$-alkyl" denotes alkyl groups with 1 to 4 carbon atoms and "$C_{1-7}$-alkyl" denotes alkyl groups with 1 to 7 carbon atoms. Examples for "alkyl" are methyl, ethyl, propyl, isopropyl, n-butyl, isobutyl, sec-butyl, tent-butyl and the like. Preferred are methyl and i-propyl.

The term "alkoxy", alone or in combination with other groups, denotes a group —O—R' wherein R' is alkyl as defined above. "$C_{1-12}$-alkoxy" denotes alkoxy groups with 1 to 12 carbon atoms, "$C_{1-4}$-alkoxy" denotes alkoxy groups with 1 to 4 carbon atoms and "$C_{1-7}$-alkoxy" denotes alkoxy groups with 1 to 7 carbon atoms. Examples for "alkoxy" are methoxy, ethoxy, propoxy, tert-butoxy and the like. Preferred is methoxy.

The term "aromatic" means the presence of an electron sextet in a ring, according to Hückel's rule.

The term "cyano" denotes the group —CN.

The term "hydroxy" denotes the group —OH.

The term "halo" or "halogen" denotes chloro, iodo, fluoro and bromo. Preferred are chloro and fluoro.

The terms "halo-$C_{1-n}$-alkyl" and "$C_{1-n}$-haloalkyl", alone or in combination with other groups, denote a $C_{1-n}$-alkyl group as defined above, with 1 to n carbon atoms as defined in the specification, wherein at least one of the hydrogen atoms of the alkyl group is replaced by a halogen atom, preferably fluoro or chloro, most preferably fluoro. Examples of halo-$C_{1-n}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-$C_{1-n}$-alkyl groups are difluoro- or trifluoro-methyl or -ethyl as well as —$CF_3$, —$CH(CH_3)CH_2CF_3$, —$CH(CH_3)CH_2F$.

The term "heterocycloalkyl", alone or in combination with other groups, as defined herein refers to a monovalent 3 to 7 membered or 4 to 7 membered saturated ring containing one or two heteroatoms selected from N, O or S. The term "3- to 7-membered heterocycloalkyl", alone or in combination with other groups, as defined herein refers to a monovalent 3 to 7 membered ring containing one or two heteroatoms selected from N, O or S. The term "4-7 membered heterocycloalkyl", alone or in combination with other groups, refers to a 4 to 7 membered saturated ring containing one or two heteroatoms selected from N, O or S. Examples for heterocycloclakyl moieties are oxetanyl, tetrahydrofuranyl, tetrahydropyranyl, pyrrolidinyl, morpholinyl, thiomorpholinyl, piperidinyl, or piperazinyl. Preferred heterocycloalkyl are oxetanyl and tetrahydrofuranyl. Heterocycloalkyl is optionally substituted as described herein.

The terms "heteroaryl", alone or in combination with other groups, refer to a monovalent aromatic 5- or 6-membered monocyclic ring ("5- or 6-membered heteroaryl") containing one or two ring heteroatoms selected from N, O, or S, the remaining ring atoms being C. 6-Membered heteroaryl are preferred. Examples for heteroaryl moieties include but are not limited to pyridinyl, pyrimidinyl, or pyrazinyl. Preferred is pyridinyl.

The term "aryl", alone or in combination with other groups, denotes a monovalent cyclic aromatic hydrocarbon moiety consisting of a mono- or bicyclic aromatic ring. Particular aryl are phenyl or naphthyl. Aryl may be unsubstituted or substituted as described herein.

The terms "cycloalkyl" and "$C_{3-7}$-cycloalkyl", alone or in combination with other groups, refer to a 3 to 7 membered carbon ring, for example cyclopropyl, cyclobutyl, cyclopentyl or cyclohexyl.

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens like the group —$SO_2$.

When indicating the number of subsituents, the term "one or more" means from one substituent to the highest possible number of substitution, i.e. replacement of one hydrogen up to replacement of all hydrogens by substituents. Thereby, one, two or three substituents are preferred. Even more preferred are one or two substituents or one substituent.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The terms "pharmaceutically acceptable carrier" and "pharmaceutically acceptable auxiliary substance" refer to carriers and auxiliary substances such as diluents or excipients that are compatible with the other ingredients of the formulation. Such a formulation is a formulation in pharmaceutically acceptable form.

The term "prodrug" refers to a structural derivative of a drug which must be chemically transformed within the body into the drug in order to exert its pharmacological or therapeutic action (see Patrick[9] or Ganellin et al.[10]).

The term "pharmaceutical composition" encompasses a product comprising specified ingredients in pre-determined amounts or proportions, as well as any product that results, directly or indirectly, from combining specified ingredients in specified amounts. In particular, it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as in particular, more particular and most particular definitions, if any.

The terms "treating", "contacting" and "reacting" when referring to a chemical reaction mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. Treatment include prophylactic treatment as well as the acute alleviation of symptoms.

The term "aromatic" denotes the conventional idea of aromaticity as defined in the literature, in particular in IUPAC[11].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

One embodiment of the invention relates to the use of a V1a antagonist for the treatment and/or prevention of phase shift sleep disorders.

One embodiment of the invention relates to the use of a V1a antagonist for the treatment of phase shift sleep disorders.

One embodiment of the invention relates to the use of a V1a antagonist for the prevention of phase shift sleep disorders.

One embodiment of the invention relates to the use of a V1a antagonist for the treatment and/or prevention of phase shift sleep disorders, wherein the phase shift sleep disorder is jetlag.

One embodiment of the invention relates to the use of a V1a antagonist for the treatment and/or prevention of phase shift sleep disorders, wherein the V1a antagonist is a compound of formula I.

wherein
$R^1$ is aryl or heteroaryl, unsubstituted or substituted with one or more substituents independently selected from A,
$R^2$ is
H,
$C_{1-12}$-alkyl, unsubstituted or substituted with one or more OH, halo, cyano or $C_{1-12}$-alkoxy,
—$(CH_2)_q$—$R^a$, wherein $R^a$ is phenyl or 5- or 6-membered heteroaryl, each unsubstituted or substituted with one or more substituents independently selected from A,
—$(CH_2)_r NR^i R^{ii}$,
—C(O)—$C_{1-12}$-alkyl, wherein $C_{1-12}$-alkyl is unsubstituted or substituted with one or more OH, halo, cyano or $C_{1-12}$-alkoxy,
—$C(O)(CH_2)_q OC(O)$—$C_{1-12}$-alkyl,
—$C(O)(CH_2)_q NR^i R^{ii}$,
—C(O)O—$C_{1-12}$-alkyl, wherein alkyl is unsubstituted or substituted with one or more OH, halo, cyano or $C_{1-12}$-alkoxy,
—$S(O)_2$—$C_{1-12}$-alkyl, or
—$S(O)_2 NR^i R^{ii}$,
$R^i$ and $R^{ii}$ are each independently H, $C_{1-12}$-alkyl, or form together with the nitrogen to which they are bound a 3- to 7-membered heterocycloalkyl containing one or two heteroatoms selected from N, O or S, which heterocycloalkyl is unsubstituted or substituted by one or more substituents independently selected from B,
q is 1, 2, 3 or 4,
r is 2, 3 or 4,
A is halo, cyano, OH, $C_{1-7}$-alkyl, halo-$C_{1-7}$-alkyl, or $C_{1-7}$-alkoxy, halo-$C_{1-7}$-alkoxy, or hydroxy-$C_{1-7}$-alkyl,
B is oxo, halo, OH, $C_{1-7}$-alkyl or $C_{1-7}$-alkoxy,
$R^3$ is Cl or F,
or a pharmaceutically acceptable salt thereof.

One embodiment of the invention relates to the use of a selective V1a antagonist for the treatment and/or prevention of phase shift sleep disorders.

One embodiment of the invention relates to the use of a selective V1a antagonist for the treatment of phase shift sleep disorders.

One embodiment of the invention relates to the use of a selective V1a antagonist for the prevention of phase shift sleep disorders.

One embodiment of the invention relates to the use of a selective V1a antagonist for the treatment and/or prevention of phase shift sleep disorders, wherein the phase shift sleep disorder is jetlag.

One embodiment of the invention relates to the use of a V1a antagonist for the treatment and/or prevention of phase shift sleep disorders, wherein $R^1$ is a monovalent cyclic aromatic hydrocarbon moiety consisting of a mono- or bicyclic aromatic ring, or a monovalent 5- or 6-membered aromatic monocyclic or 9- or 10-membered aromatic bicyclic ring containing from one to four ring heteroatoms selected from N, O, or S, the remaining ring atoms being C, each unsubstituted or substituted with one or more substituents independently selected from A; and A is halo, cyano, OH, $C_{1-7}$-alkyl, halo-$C_{1-7}$-alkyl, $C_{1-7}$-alkoxy, halo-$C_{1-7}$-alkoxy or hydroxy-$C_{1-7}$-alkyl.

One embodiment of the invention relates to the use of a V1a antagonist for the treatment and/or prevention of phase shift sleep disorders, wherein the V1a antagonist is a compound of formula I, wherein $R^1$ is a monovalent cyclic aromatic hydrocarbon moiety consisting of a mono-aromatic ring.

One embodiment of the invention relates to the use of a V1a antagonist for the treatment and/or prevention of phase shift sleep disorders, wherein the V1a antagonist is a compound of formula I, wherein wherein $R^1$ is pyridinyl.

One embodiment of the invention relates to the use of a V1a antagonist for the treatment and/or prevention of phase shift sleep disorders, wherein the V1a antagonist is a compound of formula I, wherein $R^2$ is
- H,
- $C_{1-12}$-alkyl, unsubstituted or substituted with one or more OH,
- —$(CH_2)_q$—$R^a$, wherein $R^a$ is phenyl or 5- or 6-membered heteroaryl and q is 1, 2, 3 or 4, preferably 1,
- —C(O)—$C_{1-12}$-alkyl,
- —C(O)$(CH_2)_q$NR$^i$R$^{ii}$, wherein R$^i$ and R$^{ii}$ are each independently H or $C_{1-12}$-alkyl, preferably $C_{1-12}$-alkyl, and q is 1, 2, 3 or 4, preferably 1,
- —C(O)O—$C_{1-12}$-alkyl,
- —S(O)$_2$—$C_{1-12}$-alkyl, or
- —S(O)$_2$NR$^i$R$^{ii}$, wherein R$^i$ and R$^{ii}$ are each independently H or $C_{1-12}$-alkyl, preferably $C_{1-12}$-alkyl.

One embodiment of the invention relates to the use of a V1a antagonist for the treatment and/or prevention of phase shift sleep disorders, wherein the V1a antagonist is a compound of formula I, wherein $R^2$ is methyl.

One embodiment of the invention relates to the use of a V1a antagonist for the treatment and/or prevention of phase shift sleep disorders, wherein the V1a antagonist is a compound of formula I, wherein $R^3$ is Cl.

One embodiment of the invention relates to the use of a V1a antagonist for the treatment and/or prevention of phase shift sleep disorders, wherein the V1a antagonist is a compound of formula I, wherein the compound is selected from the group consisting of trans-8-Chloro-1-(4-phenoxy-cyclohexyl)-4H,6H-2,3,5,10b-tetraaza-benzoazulene-5-carboxylic acid tert-butyl ester, trans-8-Chloro-1-(4-phenoxy-cyclohexyl)-5,6-dihydro-4H-2,3,5,10b-tetraaza-benzoazulene hydrochloride, trans-8-Chloro-5-methyl-1-(4-phenoxy-cyclohexyl)-5,6-dihydro-4H-2,3,5,10b-tetraaza-benzo[e]azulene, trans-1-[8-Chloro-1-(4-phenoxy-cyclohexyl)-4H,6H-2,3,5,10b-tetraaza-benzoazulen-5-yl]-ethanone, trans-8-Chloro-5-methanesulfonyl-1-(4-phenoxy-cyclohexyl)-5,6-dihydro-4H-2,3,5,10b-tetraaza-benzoazulene, trans-2-[8-Chloro-1-(4-phenoxy-cyclohexyl)-4H,6H-2,3,5,10b-tetraaza-benzoazulen-5-yl]-ethanol, trans-8-Chloro-5-isopropyl-1-(4-phenoxy-cyclohexyl)-5,6-dihydro-4H-2,3,5,10b-tetraaza-benzoazulene, trans-8-Chloro-1-(4-phenoxy-cyclohexyl)-4H,6H-2,3,5,10b-tetraaza-benzoazulene-5-sulfonic acid dimethylamide, trans-8-Chloro-1-(4-phenoxy-cyclohexyl)-5-pyridin-2-ylmethyl-5,6-dihydro-4H-2,3,5,10b-tetraaza-benzoazulene, trans-1-[8-Chloro-1-(4-phenoxy-cyclohexyl)-4H,6H-2,3,5,10b-tetraaza-benzoazulen-5-yl]-2-dimethylamino-ethanone, trans-8-Fluoro-1-(4-phenoxy-cyclohexyl)-4H,6H-2,3,5,10b-tetraaza-benzo[e]azulene-5-carboxylic acid tert-butyl ester, trans-8-Fluoro-5-methyl-1-(4-phenoxy-cyclohexyl)-5,6-dihydro-4H-2,3,5,10b-tetraaza-benzoazulene, cis-8-Chloro-1-(4-phenoxy-cyclohexyl)-4H,6H-2,3,5,10b-tetraaza-benzoazulene-5-carboxylic acid tert-butyl ester, cis-8-Chloro-5-methyl-1-(4-phenoxy-cyclohexyl)-5,6-dihydro-4H-2,3,5,10b-tetraaza-benzoazulene, trans-8-Chloro-1-[4-(4-fluoro-phenoxy)-cyclohexyl]-4H,6H-2,3,5,10b-tetraaza-benzoazulene-5-carboxylic acid tert-butyl ester, trans-8-Chloro-1-[4-(4-fluoro-phenoxy)-cyclohexyl]-5,6-dihydro-4H-2,3,5,10b-tetraaza-benzo[e]azulene hydrochloride, trans-8-Chloro-1-[4-(4-fluoro-phenoxy)-cyclohexyl]-5-methyl-5,6-dihydro-4H-2,3,5,10b-tetraaza-benzoazulene, trans-8-Chloro-1-[4-(4-cyano-phenoxy)-cyclohexyl]-4H,6H-2,3,5,10b-tetraaza-benzo[e]azulene-5-carboxylic acid tert-butyl ester, trans-4-[4-(8-Chloro-5-methyl-5,6-dihydro-4H-2,3,5,10b-tetraaza-benzo[e]azulen-1-yl)-cyclohexyloxy]-benzonitrile, trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester, trans-8-Chloro-1-[4-(3-chloro-phenoxy)-cyclohexyl]-4H,6H-2,3,5,10b-tetraaza-benzoazulene-5-carboxylic acid tert-butyl ester, trans-8-Chloro-1-[4-(3-chloro-phenoxy)-cyclohexyl]-5-methyl-5,6-dihydro-4H-2,3,5,10b-tetraaza-benzoazulene, trans-8-Chloro-1-[4-(3-methoxy-phenoxy)-cyclohexyl]-4H,6H-2,3,5,10b-tetraaza-benzoazulene-5-carboxylic acid tert-butyl ester, trans-8-Chloro-1-[4-(3-methoxy-phenoxy)-cyclohexyl]-5,6-dihydro-4H-2,3,5,10b-tetraaza-benzo[e]azulene hydrochloride, trans-8-Chloro-1-[4-(3-methoxy-phenoxy)-cyclohexyl]-5-methyl-5,6-dihydro-4H-2,3,5,10b-tetraaza-benzoazulene, trans-3-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-m-tolyloxy-cyclohexyl)-4H,6H-2,3,5,10b-tetraaza-benzo[e]azulene-5-carboxylic acid tert-butyl ester, trans-8-Chloro-1-(4-m-tolyloxy-cyclohexyl)-5,6-dihydro-4H-2,3,5,10b-tetraaza-benzo[e]azulene hydrochloride, trans-8-Chloro-5-methyl-1-(4-m-tolyloxy-cyclohexyl)-5,6-dihydro-4H-2,3,5,10b-tetraaza-benzo[e]azulene, trans-1-[4-(3-tert-Butyl-phenoxy)-cyclohexyl]-8-chloro-4H,6H-2,3,5,10b-tetraaza-benzo[e]azulene-5-carboxylic acid tert-butyl ester, trans-8-Chloro-1-[4-(2-fluoro-phenoxy)-cyclohexyl]-4H,6H-2,3,5,10b-tetraaza-benzo[e]azulene-5-carboxylic acid tert-butyl ester, trans-8-Chloro-1-[4-(2-fluoro-phenoxy)-cyclohexyl]-5,6-dihydro-4H-2,3,5,10b-tetraaza-benzo[e]azulene hydrochloride, trans-8-Chloro-1-[4-(2-fluoro-phenoxy)-cyclohexyl]-5-methyl-5,6-dihydro-4H-2,3,5,10b-tetraaza-benzo[e]azulene, trans-8-Chloro-1-[4-(2-cyano-phenoxy)-cyclohexyl]-4H,6H-2,3,5,10b-tetraaza-benzoazulene-5-carboxylic acid tert-butyl ester, trans-2-[4-(8-Chloro-5,6-dihydro-4H-2,3,5,10b-tetraaza-benzo[e]azulen-1-yl)-cyclohexyloxy]-benzonitrile hydrochloride, trans-2-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-o-tolyloxy-cyclohexyl)-4H,6H-2,3,5,10b-tetraaza-benzoazulene-5-carboxylic acid tert-butyl ester, trans-8-Chloro-5-methyl-1-(4-o-tolyloxy-cyclohexyl)-5,6-dihydro-4H-2,3,5,10b-tetraaza-benzoazulene, trans-8-Chloro-1-[4-(3,5-difluoro-phenoxy)-cyclohexyl]-4H,6H-2,3,5,10b-tetraaza-benzoazulene-5-carboxylic acid tert-butyl ester, trans-8-Chloro-1-[4-(3,5-difluoro-phenoxy)-cyclohexyl]-5-methyl-5,6-dihydro-4H-2,3,5,10b-tetraaza-benzoazulene,
trans-8-Chloro-1-[4-(naphthalen-2-yloxy)-cyclohexyl]-4H,6H-2,3,5,10b-tetraaza-benzoazulene-5-carboxylic acid tert-butyl ester,
trans-8-Chloro-5-methyl-1-[4-(naphthalen-2-yloxy)-cyclohexyl]-5,6-dihydro-4H-2,3,5,10b-tetraaza-benzoazulene,
trans-8-Chloro-1-[4-(pyridin-3-yloxy)-cyclohexyl]-4H,6H-2,3,5,10b-tetraaza-benzoazulene-5-carboxylic acid tert-butyl ester,
trans-8-Chloro-5-methyl-1-[4-(pyridin-3-yloxy)-cyclohexyl]-5,6-dihydro-4H-2,3,5,10b-tetraaza-benzoazulene,
trans-8-Chloro-1-[4-(5-chloro-pyridin-3-yloxy)-cyclohexyl]-4H,6H-2,3,5,10b-tetraaza-benzoazulene-5-carboxylic acid tert-butyl ester,
trans-8-Chloro-1-[4-(5-chloro-pyridin-3-yloxy)-cyclohexyl]-5-methyl-5,6-dihydro-4H-2,3,5,10b-tetraaza-benzoazulene,
trans-8-Chloro-1-[4-(pyridin-2-yloxy)-cyclohexyl]-4H,6H-2,3,5,10b-tetraaza-benzoazulene-5-carboxylic acid tert-butyl ester,
trans-8-Chloro-1-[4-(pyridin-2-yloxy)-cyclohexyl]-5,6-dihydro-4H-2,3,5,10b-tetraaza-benzoazulene hydrochloride,
trans-8-Chloro-5-methyl-1-[4-(pyridin-2-yloxy)-cyclohexyl]-5,6-dihydro-4H-2,3,5,10b-tetraaza-benzoazulene,
trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester,
trans-8-Chloro-1-[4-(6-chloro-pyridin-2-yloxy)-cyclohexyl]-5-methyl-5,6-dihydro-4H-2,3,5,10b-tetraaza-benzo[e]azulene,
trans-8-Chloro-1-[4-(5-chloro-pyridin-2-yloxy)-cyclohexyl]-5,6-dihydro-4H-2,3,5,10b-tetraaza-benzo[e]azulene hydrochloride,
trans-8-Chloro-1-[4-(5-chloro-pyridin-2-yloxy)-cyclohexyl]-5-methyl-5,6-dihydro-4H-2,3,5,10b-tetraaza-benzo[e]azulene,
trans-8-Chloro-1-[4-(pyrimidin-2-yloxy)-cyclohexyl]-4H,6H-2,3,5,10b-tetraaza-benzo[e]azulene-5-carboxylic acid tert-butyl ester,
cis-8-Chloro-1-[4-(pyrimidin-2-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrimidin-2-yloxy)-cyclohexyl]-5,6-dihydro-4H-2,3,5,10b-tetraaza-benzo[e]azulene,
trans-8-Chloro-1-[4-(pyrazin-2-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrazin-2-yloxy)-cyclohexyl]-5,6-dihydro-4H-2,3,5,10b-tetraaza-benzo[e]azulene,
trans-8-Chloro-1-[4-(pyrimidin-4-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrimidin-4-yloxy)-cyclohexyl]-5,6-dihydro-4H-2,3,5,10b-tetraaza-benzo [e]azulene,
trans-8-Chloro-1-[4-(pyridazin-3-yloxy)-cyclohexyl]-4H,6H-2,3,5,10b-tetraaza-benzo[e]azulene-5-carboxylic acid tert-butyl ester,
cis-8-Chloro-1-[4-(pyridazin-3-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyridazin-3-yloxy)-cyclohexyl]-5,6-dihydro-4H-2,3,5,10b-tetraaza-benzo[e]azulene,
cis-8-Chloro-1-[4-(pyridin-2-yloxy)-cyclohexyl]-4H,6H-2,3,5,10b-tetraaza-benzo[e]azulene-5-carboxylic acid tert-butyl ester,
cis-8-Chloro-1-[4-(pyridin-2-yloxy)-cyclohexyl]-5,6-dihydro-4H-2,3,5,10b-tetraaza-benzo[e]azulene,
cis-8-Chloro-5-methyl-1-[4-(pyridin-2-yloxy)-cyclohexyl]-5,6-dihydro-4H-2,3,5,10b-tetraaza-benzo[e]azulene,
trans-8-Chloro-1-[4-(3-fluoro-pyridin-2-yloxy)-cyclohexyl]-5,6-dihydro-4H-2,3,5,10b-tetraaza-benzo[e]azulene,
trans-8-Chloro-1-[4-(3-fluoro-pyridin-2-yloxy)-cyclohexyl]-5-methyl-5,6-dihydro-4H-2,3,5,10b-tetraaza-benzo[e]azulene,
trans-8-Chloro-1-[4-(5-fluoro-pyridin-2-yloxy)-cyclohexyl]-5,6-dihydro-4H-2,3,5,10b-tetraaza-benzo[e]azulene
trans-8-Chloro-1-[4-(5-fluoro-pyridin-2-yloxy)-cyclohexyl]-5-methyl-5,6-dihydro-4H-2,3,5,10b-tetraaza-benzo[e]azulene,
trans-8-Chloro-1-[4-(6-methyl-pyridin-2-yloxy)-cyclohexyl]-5,6-dihydro-4H-2,3,5,10b-tetraaza-benzo[e]azulene,
trans-8-Chloro-5-(2,2-difluoro-ethyl)-1-[4-(6-methyl-pyridin-2-yloxy)-cyclohexyl]-5,6-dihydro-4H-2,3,5,10b-tetraaza-benzo[e]azulene,
trans-8-Chloro-5-(2-fluoro-ethyl)-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(3-fluoro-pyridin-2-yloxy)-cyclohexyl]-5,6-dihydro-4H-2,3,5,10b-tetraaza-benzo[e]azulene,
trans-8-Chloro-5-ethyl-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(6-methyl-pyridin-2-yloxy)-cyclohexyl]-5,6-dihydro-4H-2,3,5,10b-tetraaza-benzo[e]azulene, and
trans-8-Chloro-5-methyl-1-[4-(6-methyl-pyridin-2-yloxy)-cyclohexyl]-5,6-dihydro-4H-2,3,5,10b-tetraaza-benzo[e]azulene.

One embodiment of the invention relates to the use of a V1a antagonist for the treatment and/or prevention of phase shift sleep disorders, wherein the V1a antagonist is example 1

One embodiment of the invention relates to a method for the treatment and/or prevention of phase shift sleep disorders in a subject in need of such treatment, which comprises administering to said subject a therapeutically effective amount of a V1a antagonist of formula I as described herein.

One embodiment of the invention relates to a method for the treatment and/or prevention of phase shift sleep disorders in a subject in need of such treatment, which comprises administering to said subject a therapeutically effective amount of a V1a antagonist.

One embodiment of the invention relates to a pharmaceutical composition comprising a V1a antagonist in a pharmaceutically acceptable form.

One embodiment of the invention relates to a pharmaceutical composition comprising a V1a antagonist of formula I as described herein in a pharmaceutically acceptable form.

One embodiment of the invention relates to a pharmaceutical composition comprising a V1a antagonist of formula I as described herein in a pharmaceutically acceptable form for the treatment and/or prevention of phase shift sleep disorders.

One embodiment of the invention relates to a pharmaceutical composition comprising a V1a antagonist in a pharmaceutically acceptable form for the treatment and/or prevention of phase shift sleep disorders.

One embodiment of the invention relates to a V1a antagonist of formula I as described herein for use in the treatment and/or prevention of phase shift sleep disorders.

One embodiment of the invention relates to a selective V1a antagonist of formula I as described herein, which is example 1 for use in the treatment and/or prevention of phase shift sleep disorders.

One embodiment of the invention relates to a selective V1a antagonist of formula I as described herein, which is example 1 for use in the treatment and/or prevention of jet lag.

One embodiment of the invention relates to a V1a antagonist for use in the treatment and/or prevention of phase shift sleep disorders.

One embodiment of the invention relates to a V1a antagonist for use in the preparation of medicaments for the treatment and/or prevention of phase shift sleep disorders.

One embodiment of the invention relates to a V1a antagonist of formula I as described herein for use in the preparation of medicaments for the treatment and/or prevention of phase shift sleep disorders.

One embodiment of the invention relates to a selective V1a antagonist of formula I as described herein for use in the treatment and/or prevention of phase shift sleep disorders.

One embodiment of the invention relates to a selective V1a antagonist for use in the treatment and/or prevention of phase shift sleep disorders.

One embodiment of the invention relates to a selective V1a antagonist for use in the preparation of medicaments for the treatment and/or prevention of phase shift sleep disorders.

One embodiment of the invention relates to a selective V1a antagonist of formula I as described herein for use in the preparation of medicaments for the treatment and/or prevention of phase shift sleep disorders.

One embodiment of the invention relates to the use of a V1a antagonist for the preparation of medicaments for the treatment and/or prevention of phase shift sleep disorders.

One embodiment of the invention relates to the use of a V1a antagonist of formula I as described herein for the preparation of medicaments for the treatment and/or prevention of phase shift sleep disorders.

Pharmaceutical Composition

A compound of formula I as well as their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

A compound of formulae I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formulae I should be appropriate, although the above upper limit can also be exceeded when necessary.

Examples of compositions according to the invention are, but are not limited to:

EXAMPLE A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I-III, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

A compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

A compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

1) Material and Methods

In all studies described below, male young-adult C57BL/6J mice (4 weeks old at the beginning of experiments) were used. Animals were exposed to a light-dark cycle (LD) 12:12 (lights on from 8 h to 20 h geographical time; light intensity at 200 lux; during dark period dim red light of 5 lux) in individual cages with food and water ad libitum and temperature (22±1° C.) and humidity (55%±5%) controlled. LD cycle was represented as zeitgeber times (ZT) where ZT0 represents the lights on and ZT12 lights off. When animals were exposed to constant darkness conditions (DD), circadian times (CT) were used as time point references, where CT12 corresponds to activity onset.

Characterization of Behavioural Circadian Responses to the Specific V1a Antagonist trans-8-chloro-5-methyl-1-(4-pyridin-2-yloxycyclohexyl)-4,6-dihydro-[1,2,4]triazolo[4,3-a][1,4]benzodiazepine (Example 1) in Mice (ZT12 and ZT0)

It was evaluated whether there is a phase window of sensitivity to the V1a receptor antagonist trans-8-chloro-5-methyl-1-(4-pyridin-2-yloxycyclohexyl)-4,6-dihydro-[1,2,4]triazolo[4,3-a][1,4]benzodiazepine (example 1). A group of animals was treated at 2 temporal points (one during the day and one at night). Animals were exposed to LD cycle conditions (at least for 10 days) to obtain a baseline of the rhythm of locomotor activity. 4 groups were selected: (group 1) Sham manipulations, animals into which the cannula was introduced in the oral cavity without any solution delivery; (group 2) vehicle, and (groups 2 and 3) administration of the V1a receptor antagonist trans-8-chloro-5-methyl-1-(4-pyridin-2-yloxycyclohexyl)-4,6-dihydro-[1,2,4]triazolo[4,3-a][1,4]benzodiazepine (doses of 10 mg/kg and 30 mg/kg). Administrations were performed (orally) at ZT/CT12 (lights off/activity onset; sham, n=5; vehicle n=5; 10 mg/kg n=5; and 30 mg/kg n=5). After the first manipulation at ZT/CT12, animals were immediately exposed to DD conditions and remained at least for 10 days more for behavioural analysis, and then re-entrained to a 12-12 LD cycle, for a minimum of 10 days, to be re-exposed to the second experimental manipulation at ZT/CT0 (lights on/activity offset; sham, n=3; vehicle n=3; 10 mg/kg n=5; and 30 mg/kg n=5).

Characterization of Behavioural Circadian Responses to the Specific V1a Antagonist trans-8-chloro-5-methyl-1-(4-pyridin-2-yloxycyclohexyl)-4,6-dihydro-[1,2,4]triazolo[4,3-a][1,4]benzodiazepine (Example 1) in mice (ZT18 and ZT6)

A new group of animals was treated at another 2 temporal points different from the previous experiment; ZT/CT6 (6 h after lights on/mid rest period; sham, n=3; vehicle n=4; and 30 mg/kg n=5) and ZT/CT18 (6 h after lights off/mid activity period; sham, n=3; vehicle n=4; and 30 mg/kg n=5). For this experiment (time points ZT/CT6 and ZT/CT18), trans-8-chloro-5-methyl-1-(4-pyridin-2-yloxycyclohexyl)-4,6-dihydro-[1,2,4]triazolo[4,3-a][1,4]benzodiazepine was administrated only at the 30 mg/kg dose. Thus, 3 groups were selected: (Group 1) Sham manipulations, (Group 2) vehicle administrations and (Group 3) trans-8-chloro-5-methyl-1-(4-pyridin-2-yloxycyclohexyl)-4,6-dihydro-[1,2,4]triazolo[4,3-a][1,4]benzodiazepine (30 mg/kg). After manipulations, animals were immediately exposed to DD conditions and remained at least for 10 days more for behavioural analysis, and then re-entrained to a 12-12 LD cycle for a minimum of 10 days.

Effects of V1a Antagonist trans-8-chloro-5-methyl-1-(4-pyridin-2-yloxycyclohexyl)-4,6-dihydro-[1,2,4]triazolo[4,3-a][1,4]benzodiazepine on Light Synchronization of the Clock in Mice To evaluate the effects of the V1a antagonist trans-8-chloro-5-methyl-1-(4-pyridin-2-yloxycyclohexyl)-4,6-dihydro-[1,2,4]triazolo[4,3-a][1,4]benzodiazepine on light synchronization of behavioural circadian rhythms, a jet-lag protocol of 6 h phase shift was used. After being under a LD cycle 12 h/12 h (for at least 10 days), mice were exposed to a 6-h phase advance of the light-dark cycle (first "jet-lag" test, advance shift) and to the administration of vehicle or 30 mg/kg of the V1a antagonist trans-8-chloro-5-methyl-1-(4-pyridin-2-yloxycyclohexyl)-4,6-dihydro-[1,2,4]triazolo[4,3-a][1,4]benzodiazepine. On the day of the shift, the time of lights off was phase-advanced by 6 h. Here we used three groups of animals: a sham group (Group 1, n=3), animals in which the cannula was introduced in the oral cavity without any solution delivery; a vehicle group (Group 2, n=4), which received vehicle, and a 30 mg/kg trans-8-chloro-5-methyl-1-(4-pyridin-2-yloxycyclohexyl)-4,6-dihydro-[1,2,4]triazolo[4,3-a][1,4]benzodiazepine group (Group 3, n=5). All manipulations were at ZT6 (6 h after lights on) on the last LD cycle before the 6 h phase advance.

In a second experiment, using naive animals, a second jet-lag test was evaluated. Thus, using a new group of male mice, the effects of 30 mg/kg trans-8-chloro-5-methyl-1-(4-pyridin-2-yloxycyclohexyl)-4,6-dihydro-[1,2,4]triazolo[4,3-a][1,4]benzodiazepine on the re-synchronization to a 6 h phase advance of the LD cycle were tested. Animals under a LD cycle 12 h/12 h (for at least 10 days) were exposed to a phase advance of 6 h of the LD cycle and to the administration of vehicle or 30 mg/kg of the V1a antagonist trans-8-chloro-5-methyl-1-(4-pyridin-2-yloxycyclohexyl)-4,6-dihydro-[1,2,4]triazolo[4,3-a][1,4]benzodiazepine at ZT/CT6. Similarly to the previous experiment, three groups of animals were used: a sham group (Group 1, n=3), animals in which the cannula was introduced in the oral cavity without any solution delivery; a vehicle group (Group 2, n=4) which received vehicle, and a 30 mg/kg trans-8-chloro-5-methyl-1-(4-pyridin-2-yloxycyclohexyl)-4,6-dihydro-[1,2,4]triazolo[4,3-a][1,4]benzodiazepine group (Group 3, n=5).

Behavioural Recording and Analysis

The locomotor activity rhythms were measured using infra-red detectors on the top of the cages and/or running wheels. Activity data were displayed as actograms using the program ClockLab (Actimetrics, Evanston, Ill., USA), and the following parameters were analyzed:

Phase shifts: Phase shifts were measured by fitting two regression lines to the onsets of locomotor activity for 10 days before and 10 days after the manipulation (ClockLab; Actimetrics, Evanston, Ill., USA). A computer algorithm was used to identify the onset of the main period of daily locomotor activity (ClockLab). The data collected on the day following the manipulation (sham, vehicle or drug administration) was excluded from the line fits to ensure that the circadian phase was in steady state. Phase shift was defined as the difference (in hours) between the pre-stimulus line and the post-stimulus line. The magnitude of the phase shifts was fitted by linear regression to the onsets, considering 10 cycles before (LD) and 10 cycles after compound administration when animals were released in constant darkness (DD; Aschoff Type II procedure to evaluate phase shifts; Mrosovsky, 1996b).

Period: Endogenous periods were determined by an analysis of $\chi^2$ periodogram (ClockLab).

Alpha: Also the duration of the active period (alpha) before and after treatments was calculated. For that, using the program ClockLab, both the onset and offset of activity (in both LD and DD) were determined. The difference (in hours) between these two reference points represents alpha or the duration of activity period. The onsets and offsets of activity were identified automatically using the ClockLab software.

Activity profiles: Activity data were collected into 30-minute bins and plotted as waveforms averaging 6-h of activity (day of drug administration) of animals after manipulations using ClockLab. Group mean average waveforms of activity were obtained from the 6-h of activity after manipulations from each animal.

Re-entrainment (jet-lag tests): For 6 h phase-shift (jet-lag protocol) the number of days after the shift for total re-entrainment was quantified, considering both the onset and offset of activity. The onsets and offsets of activity were identified automatically using ClockLab software. Thus, full resynchronization to a new LD cycle, after 6-hour phase shifts of the time of lights off, was considered when activity onset took place at the new time of lights off ±30 minutes. The number of days (transitory cycles) required to re-synchronize was calculated for each mouse. The speed of re-entrainment was evaluated calculating the onset of activity and the advance of it, in hours, daily. To evaluate the effects of manipulations on locomotion, the locomotor activity changes from 0 to 6 h after each treatment were quantified in 30 min intervals (see activity profiles determination).

Statistical Analysis

Values in all experiments are means ±SEM. Statistical comparisons were performed using one way analysis of variance (ANOVA) for both independent (phase-shifts, period, re-entrainment) and repeated measures (activity profiles, alpha) followed with post hoc Fisher's (LSD) test. The critical value of significance was p<0.05 for all experiments. The statistical package Statistica (version 8.0) was used.

Results

Phase-shift, Period, Alpha and Activity Profiles of Behavioural Circadian Rhythms to trans-8-chloro-5-methyl-1-(4-pyridin-2-yloxycyclohexyl)-4,6-dihydro-[1,2,4]triazolo[4,3-a][1,4]benzodiazepine (Example 1) Administrations at ZT/CT12 and ZT/CT0

For the first part of the experiment at the two time points tested, ZT/CT12 and ZT/CT0, two doses of the V1a receptor antagonist trans-8-chloro-5-methyl-1-(4-pyridin-2-yloxycyclohexyl)-4,6-dihydro-[1,2,4]triazolo[4,3-a][1,4]benzodiazepine, 10 mg/kg and 30 mg/kg, were used.

Evaluations of behavioural phase-shifts after a single administration of the V1a antagonist at 10 mg/kg or 30 mg/kg showed no effect on the circadian phase (ZT/CT12, $F_{3, 16}$=0.55, p=0.65; ZT/CT0, $F_{3, 12}$=0.14, p=0.93; FIG. 1).

No significant locomotor activity change was measured after administration of the V1a antagonist at 10 mg/kg or 30 mg/kg. There was also no changes in the endogenous period of locomotor activity in animals treated at ZT/CT12 and ZT/CT0 (ZT/CT12, $F_{3, 16}$=0.4, p=0.72; ZT/CT0, $F_{3, 12}$=0.3, p=0.8; FIG. 2).

Whereas animals treated at ZT/CT12 did show changes in alpha after treatment (Pre vs. Pos-time, $F_{1, 16}$=34.5, p=0.00002), no differences between groups were observed (Groups, $F_{3, 16}$=0.08, p=0.96). Mice receiving the V1a antagonists at both 10 and 30 mg/kg doses at ZT/CT0 showed also an increase in alpha (Pre vs. Post-time, $F_{1, 12}$=81.8, p=0.000001). Despite the alpha increases of almost 2 h in V1a antagonist treated animals, this effect was not statistically significant ($F_{3, 12}$=1.48, p=0.26).

Phase-shift, Period, Alpha and Activity Profiles of Behavioural Circadian Rhythms to trans-8-chloro-5-methyl-1-(4-pyridin-2-yloxycyclohexyl)-4,6-dihydro-[1,2,4]triazolo[4,3-a][1,4]benzodiazepine (Example 1) Administrations at ZT/CT18 and ZT/CT6

Since no effect on phase-shift, period and alpha was found with the dose of 10 mg/kg, for the second part of the experiment animals received only the vehicle or the 30 mg/kg concentration of trans-8-chloro-5-methyl-1-(4-pyridin-2-yloxycyclohexyl)-4,6-dihydro-[1,2,4]triazolo[4,3-a][1,4]benzodiazepine at ZT/CT18 (mid activity period) or ZT/CT6 (mid rest period).

Animals were treated at ZT/CT18 with a sham manipulation, a vehicle administration or a 30 mg/kg dose of trans-8-chloro-5-methyl-1-(4-pyridin-2-yloxycyclohexyl)-4,6-dihydro-[1,2,4]triazolo[4,3-a][1,4]benzodiazepine. Evaluations of behavioural phase shifts after a single administration of the V1a antagonist at 30 mg/kg showed no significant effect on the circadian phase at ZT/CT18 ($F_{2, 9}$=0.13, p=0.87; nor at ZT/CT6 ($F_{2, 9}$=0.96, p=0.41; FIG. 1).

The endogenous period of locomotion is also not significantly different between groups at ZT/CT18 and ZT/CT6 (ZT/CT18, $F_{2, 9}$=0.1, p=0.9; ZT/CT6, $F_{2, 9}$=3, p=0.12; FIG. 2).

Animals treated at ZT/CT18 or ZT/CT6 showed changes in alpha after treatment (ZT/CT18, Pre vs. Post-time, $F_{1, 9}$=26.13, p=0.0006; ZT/CT6 Pre vs. Post-time, $F_{1, 9}$=52.31 p=0.00004), however, no differences between groups were observed (ZT/CT18 Groups, $F_{2, 9}$=1.35, p=0.3; ZT/CT6, $F_{2, 9}$=2.4, p=0.14).

Behavioural Re-entrainment to 6 h Phase-shift of the LD Cycle: Effects of trans-8-chloro-5-methyl-1-(4-pyridin-2-yloxycyclohexyl)-4,6-dihydro-[1,2,4]triazolo[4,3-a][1,4]benzodiazepine (Example 1) Administrations (Jet-lag Test 1)

It was demonstrated that the specific V1a antagonist is affecting light synchronization in animals exposed to an experimental phase-shift protocol.

Figure 1A:
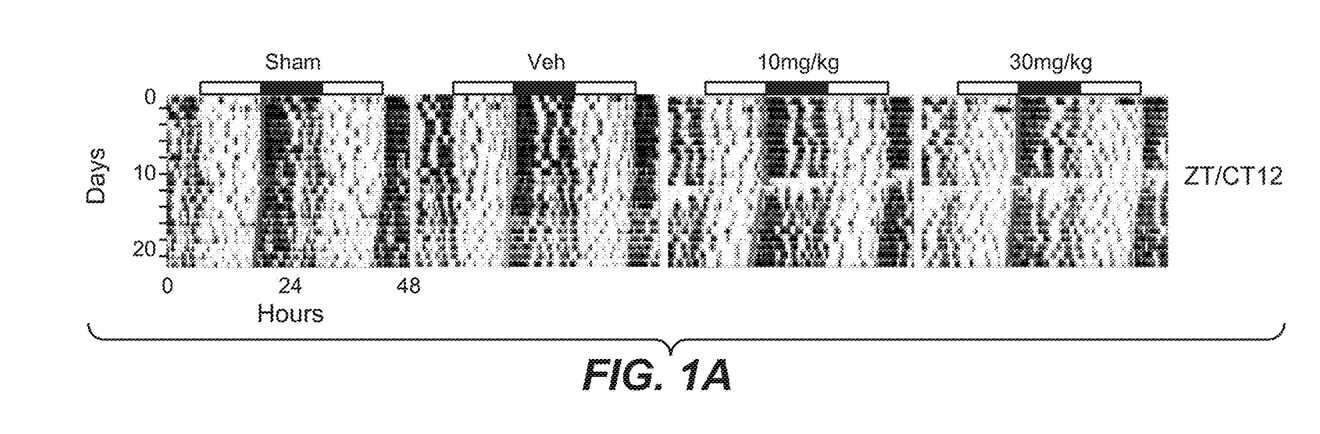
Figure 1B:
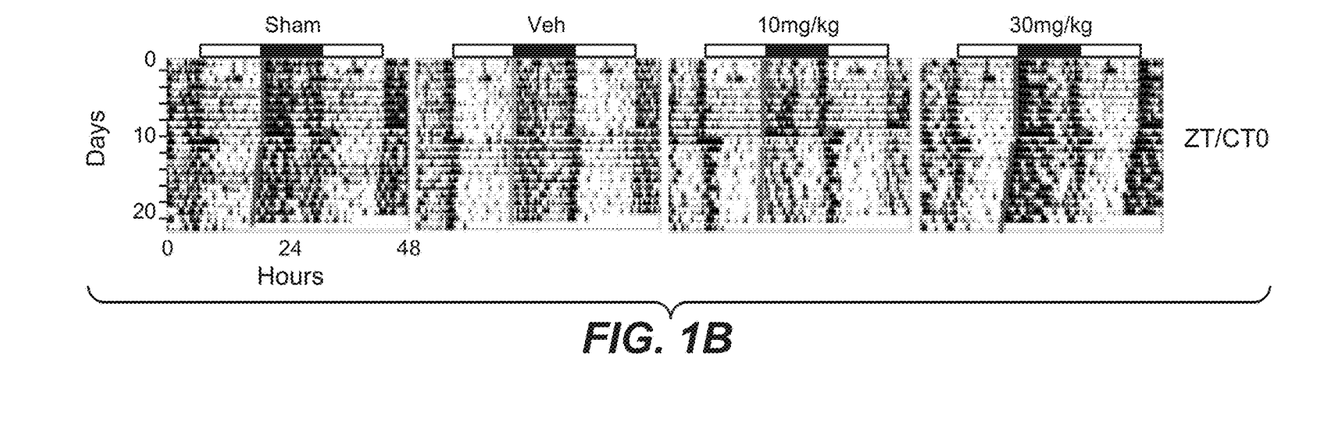
Figure 1C:
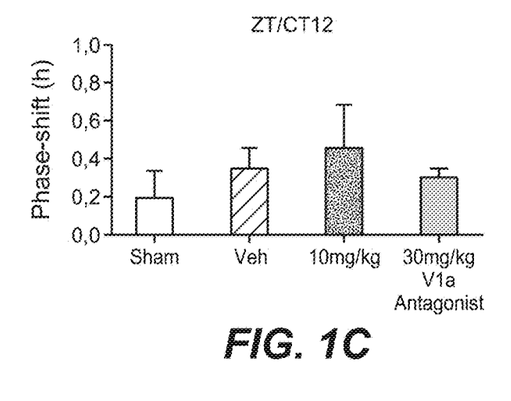
Figure 1D:
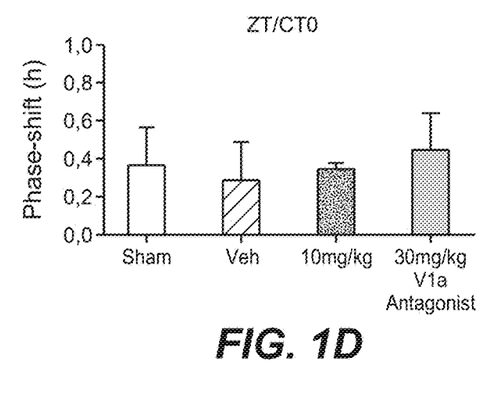
Figure 1E:
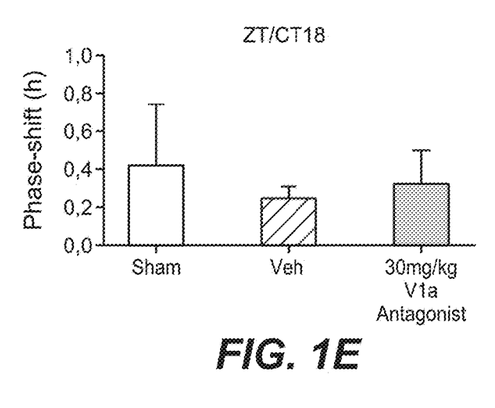
Figure 1F:
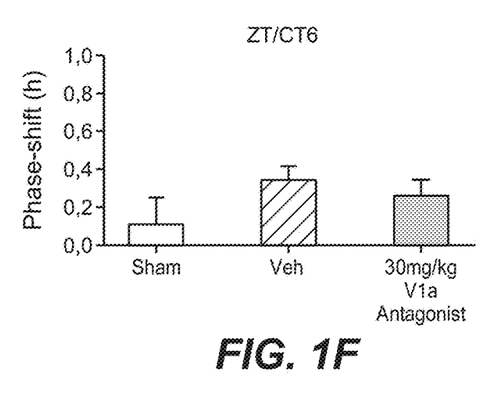
Figure 2A:
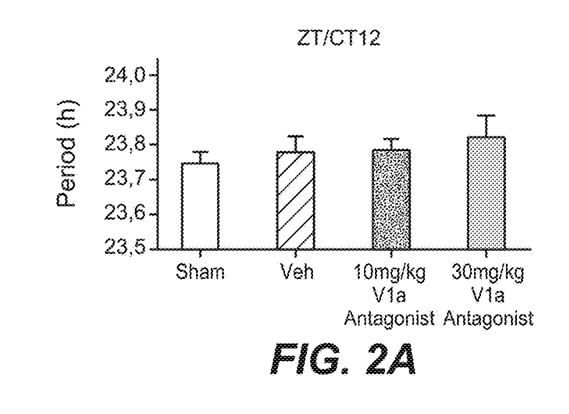
Figure 2B:
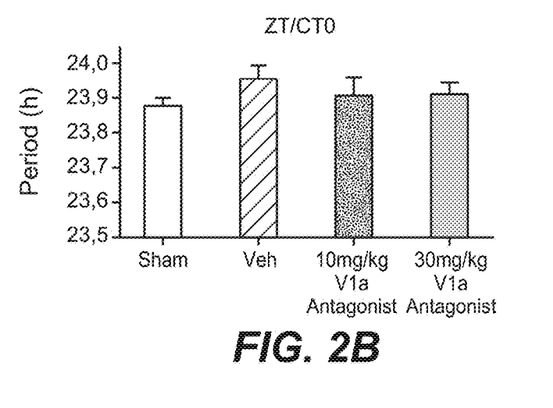
Figure 2C:
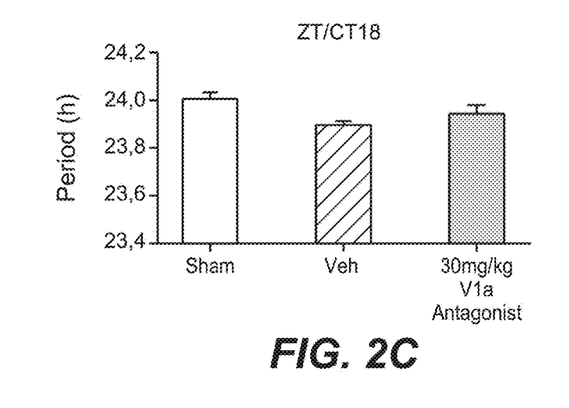
Figure 2D:
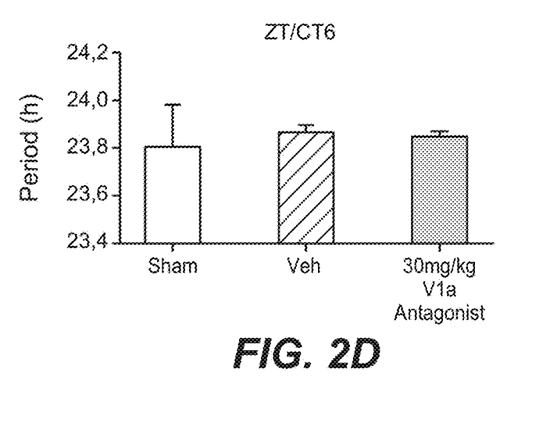
Figure 3A:
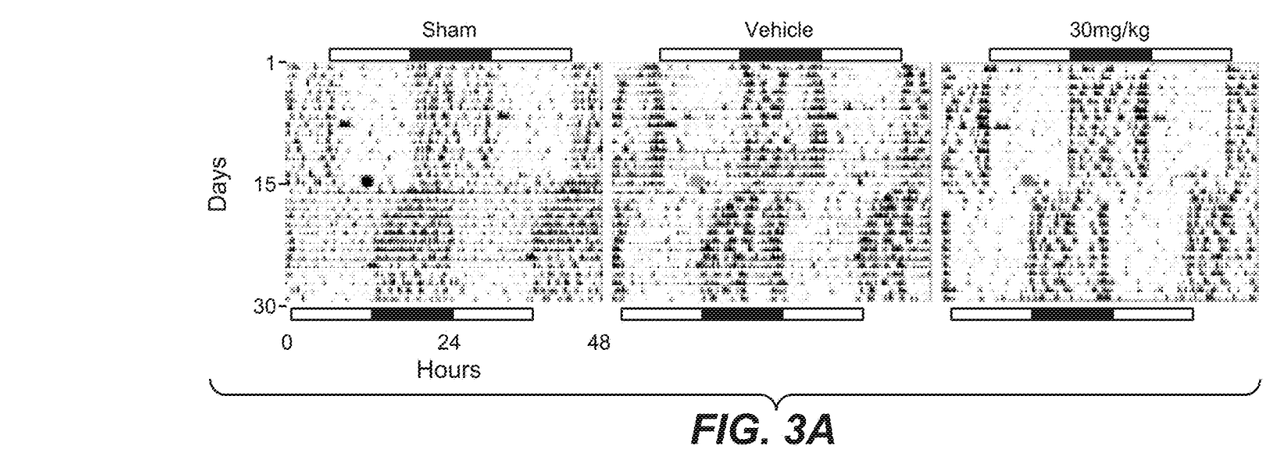
Figure 3B:
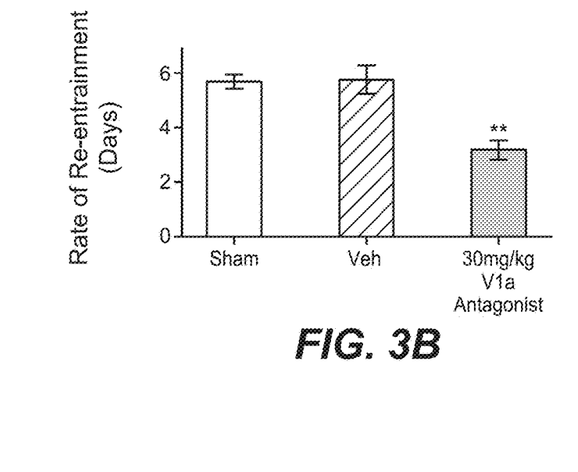
Figure 3C:
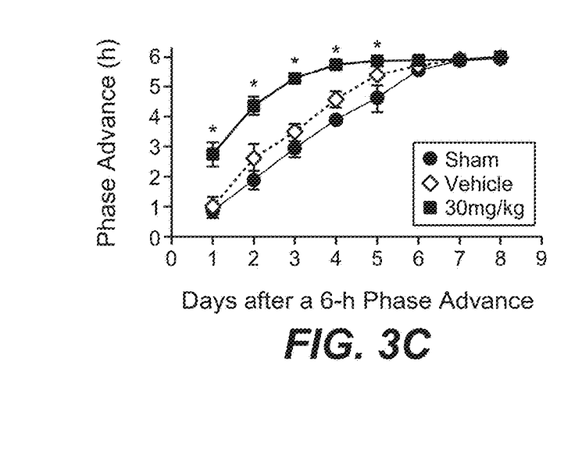

Thus, animals (sham, vehicle and V1a antagonist groups) exposed to a 6-h phase-advance of the light-dark cycle were treated with vehicle control administrations or 30 mg/kg of the V1a antagonist at ZT6 (6h after lights on) on the last day from the first LD cycle. Animals from the control sham group spent 5.66±0.27 days to entrain to the new LD cycle. Animals receiving the vehicle administration took 5.75±0.54 days to re-entrain to the new LD cycle. In contrast, mice which were treated with 30 mg/kg of the V1a receptor antagonist trans-8-chloro-5-methyl-1-(4-pyridin-2-yloxycyclohexyl)-4,6-dihydro-[1,2,4]triazolo[4,3-a][1,4]benzodiazepine took only 3.2 ±0.33 days to show a total behavioural re-entrainment after the 6 h phase shift. This effect was statistically significant ($F_{2, 9}$=10.1, p=0.005; FIG. 3). The onset of activity showed a much more rapid daily adjustment to the LD cycle for the first 5 days after the shift in the group receiving the V1a antagonist trans-8-chloro-5-methyl-1-(4-pyridin-2-yloxycyclohexyl)-4,6-dihydro-[1,2,4]triazolo[4,3-a][1,4]benzodiazepine ($F_{2, 9}$=25, p=0.0002). Locomotor activity induced by manipulations was not significantly different between groups ($F_{2, 9}$=1.25, p=0.32).

The first experiment was repeated under the same experimental conditions, but using new naive mice (young adult male mice without previous exposure to any kind of manipulation).

Naive animals from the control sham group took 5.33±0.88 days to entrain to the new LD cycle. Animals receiving the vehicle administration took 5.5±0.64 days to re-entrain to the new LD cycle. Similarly to the first phase-shift experiment, mice treated with 30 mg/kg of the V1a antagonist trans-8-chloro-5-methyl-1-(4-pyridin-2-yloxycyclohexyl)-4,6-dihydro-[1,2,4]triazolo[4,3-a][1,4]benzodiazepine took only 3.4±0.24 days to show a total behavioural re-entrainment after the 6 h phase shift. This effect was statistically significant ($F_{2, 9}$=4.99, p=0.03;FIG. 4). The onset of activity showed a much more rapid daily adjustment to the LD cycle for the first 4 days after the shift in the group treated with the V1a antagonist trans-8-chloro-5-methyl-1-(4-pyridin-2-yloxycyclohexyl)-4,6-dihydro-[1,2,4]triazolo[4,3-a][1,4]benzodiazepine ($F_{2, 9}$=14, p=0.001).

The three experimental manipulations (sham, vehicle and compound administrations) induced an increase in locomotion which was not significantly different between groups ($F_{2, 9}$=2.91, p=0.10).

Both experiments indicate that the V1a antagonist trans-8-chloro-5-methyl-1-(4-pyridin-2-yloxycyclohexyl)-4,6-dihydro-[1,2,4]triazolo[4,3-a][1,4]benzodiazepine accelerates the re-entrainment of the circadian clock to a new LD cycle.

2) Materials and Methods

Preparation of Test Compounds

The test compound was initially dissolved in DMSO at a concentration of 10 mM. Subsequent dilutions were made in assay buffer with a maximum final concentration of 0.2% DMSO.

Radioligand Binding Assay Membrane Preparation

Recombinant vasopressin $V_{1a}$ (human: $hV_{1a}$; mouse: $mV_{1a}$), $V_{1b}$ (human: $hV_{1b}$) were independently expressed in human embryonic kidney (HEK) cells using transient transfection. The cell membranes expressing the various receptors were prepared by homogenizing (using Polytron homogenizer) the cell culture pellet in lysis buffer (50 mM HEPES, 1 mM EDTA, 10 mM $MgCl_2$, pH 7.4 with protease inhibitors), then centrifuging the resulting suspension at 500 g for 20 min at 4° C. The supernatant was subsequently re-centrifuged at 43,000 g for 1 hour at 4° C. The resulting pellet was re-suspended in lysis buffer and 10% Sucrose. The concentration of protein was determined, and the membranes were aliquoted and stored at −80° C. until further use.

Radioligand Binding Assays to Assess the Affinity of Test Compound for Vasopressin Receptors from Different Species All radioligand binding assays were carried out in 96-well plates in the presence of 1 nM $^3$H-AVP (vasopressin) radioligand, and 10 concentrations of test compound (ranging from 27 μM-1 nM or 2.7 μM-0.1 nM for $hV_{1a}$ binding). Dilutions of compound were made using a Beckman Biomek 2000 laboratory automation workstation, in assay buffer. Non-specific binding was defined using 4.2 μM cold vasopressin. Each well contained membrane protein (varying concentrations), 0.5 mg of Ysi-poly-1-lysine SPA beads (only for the human receptor SPA assays not the mouse V1a filtration assay) in a final volume of 200 μl of buffer A containing: Tris 50 mM, NaCl 120 mM, KCl 5 mM, $CaCl_2$ 2 mM, $MgCl_2$ 10 mM, 1 mM Cystein (pH 7.4). All assays were conducted in duplicate and repeated at least two times. Assay plates were incubated for 1 hour at room temperature before centrifugation for human receptors (SPA) or filtration for the mouse receptor. Filtration assays were terminated by rapid filtration under vacuum through GF/C filters, pre-soaked for 5 min with buffer B containing Tris 50 mM, MgCl2 5 mM, 0.1% BSA (pH 7.4), followed by 5×0.4 ml washes of ice-cold buffer B. For both SPA and filtration plates, bound ligand was determined using a Packard Top-count scintillation counter. Saturation binding experiments performed for each assay indicated that a single homogenous population of binding sites was being labelled.

Radioligand Binding Data Calculation.

The CPM value for each duplicate of a concentration of competing compound was averaged (y1) then the % specific binding calculated, (((y1−non-specific)/(total binding-non-specific))×100). Graphs were plotted with the % specific binding using XLfit, a curve fitting program that iteratively plots the data using Levenburg Marquardt algorithm. The single site competition analysis equation used was y=A+((B−A)/(1+((x/C)$^D$))), where y is the % specific binding, A is the minimum y, B is the maximum y, C is the IC50, x is the $\log_{10}$ of the concentration of the competing compound and D is the slope of the curve (the Hill Coefficient). From these curves the IC50 (inhibition concentration at which 50% specific binding of the radioligand was displaced) and Hill coefficient were determined. The affinity constant (Ki) was calculated using the Cheng-Prussoff equation Ki=(IC50/1+([L]/Kd), where [L] is the concentration of radioligand and Kd is the equilibrium dissociation constant of the radioligand. The Ki was also expressed logarithmically as a pKi.

Results

TABLE 1

The affinity of example 1 at human and mouse $V_{1a}$, and human $V_{1b}$ receptors in radioligand binding assays

|  | $V_{1a}$ | $V_{1b}$ |
|---|---|---|
| pKi |  |  |
| Human | 9.11 ± 0.05 (5) | <4.5 (2) |
| Mouse | 7.11 ± 0.009 (3) | n.t. |
| Ki [nM] |  |  |
| Human | 0.7 ± 0.1 (5) | >27'000 (2) |
| Mouse | 77 ± 2 (3) | n.t. |

Data represents the pKi±SEM (n) or Ki [nM]±SEM (n), where the pKi is −$\log_{10}$ of the affinity constant (Ki) [M], SEM the standard error of mean, n the number of assays, (n.t. is not tested).

Example 1 trans-8-chloro-5-methyl-1-(4-pyridin-2-yloxycyclohexyl)-4,6-dihydro-[1,2,4]triazolo[4,3-a][1,4]benzodiazepine (trans-8-Chloro-5-methyl-1-[4-(pyridin-2-yloxy)-cyclohexyl]-5,6-dihydro-4H-2,3,5,10b-tetraaza-benzoazulene)

example 1

Compounds of formula I, especially example 1, can be prepared as described in PCT application WO2010/060836.

FIG. 1: (Top) Representative actograms of the locomotor activity of the different groups treated at ZT/CT12 (activity onset) or ZT0/CT0 (activity offset). Dots in actograms represent time of manipulation, and yellow and black bars on the top indicate the light and dark period, respectively. (Middle) Mean±SEM of phase-shifts of the rhythm of locomotor activity of mice treated at ZT/CT12 (activity onset; sham, n=5; vehicle n=5; 10 mg/kg n=5; 30 mg/kg n=5) or ZT/CT0 (activity offset; sham, n=3; vehicle n=3; 10 mg/kg n=5; 30 mg/kg n=5). (Bottom) Mean values (±SEM) of the phase-shifts of the rhythm of locomotor activity of mice (under the different experimental conditions) treated at ZT/CT18 (sham, n=3; vehicle n=4; 30 mg/kg n=5) or ZT/CT6 (sham, n=3; vehicle n=4; 30 mg/kg n=5).

FIG. 2: Mean values (±SEM) of the endogenous period of locomotor activity in mice under constant darkness conditions after each experimental treatment at ZT/CT12 (activity onset; sham, n=5; vehicle n=5; 10 mg/kg n=5; 30 mg/kg n=5), ZT0/CT0 (activity offset; sham, n=3; vehicle n=3; 10 mg/kg n=5; 30 mg/kg n=5), ZT/CT18 (midnight; sham, n=3; vehicle n=4; 30 mg/kg n=5) and ZT/CT6 (midday; sham, n=3; vehicle n=4; 30 mg/kg n=5).

FIG. 3: (Top) (Top) Representative actograms of the locomotor activity of the different groups treated at ZT/CT6 (mid rest period) and exposed to a 6 h phase advance shift of the LD cycle. Dots in actograms represent time of manipulation, and yellow and black bars on the top and bottom indicate the light and dark period, respectively. (Middle) Rate of re-entrainment (number of days) to show full synchronization to the new LD cycle (sham n=3, vehicle n=4, 30 mg/kg n=5). The speed of entrainment was evaluated daily. From day 1 to 5 the 30 mg/kg group treatet with the V1a antagonist trans-8-chloro-5-methyl-1-(4-pyridin-2-yloxycyclohexyl)-4,6-dihydro-[1,2,4]triazolo[4,3-a][1,4]benzodiazepine showed a significantly faster re-entrainment.

Figures 4A, 4B, 4C:
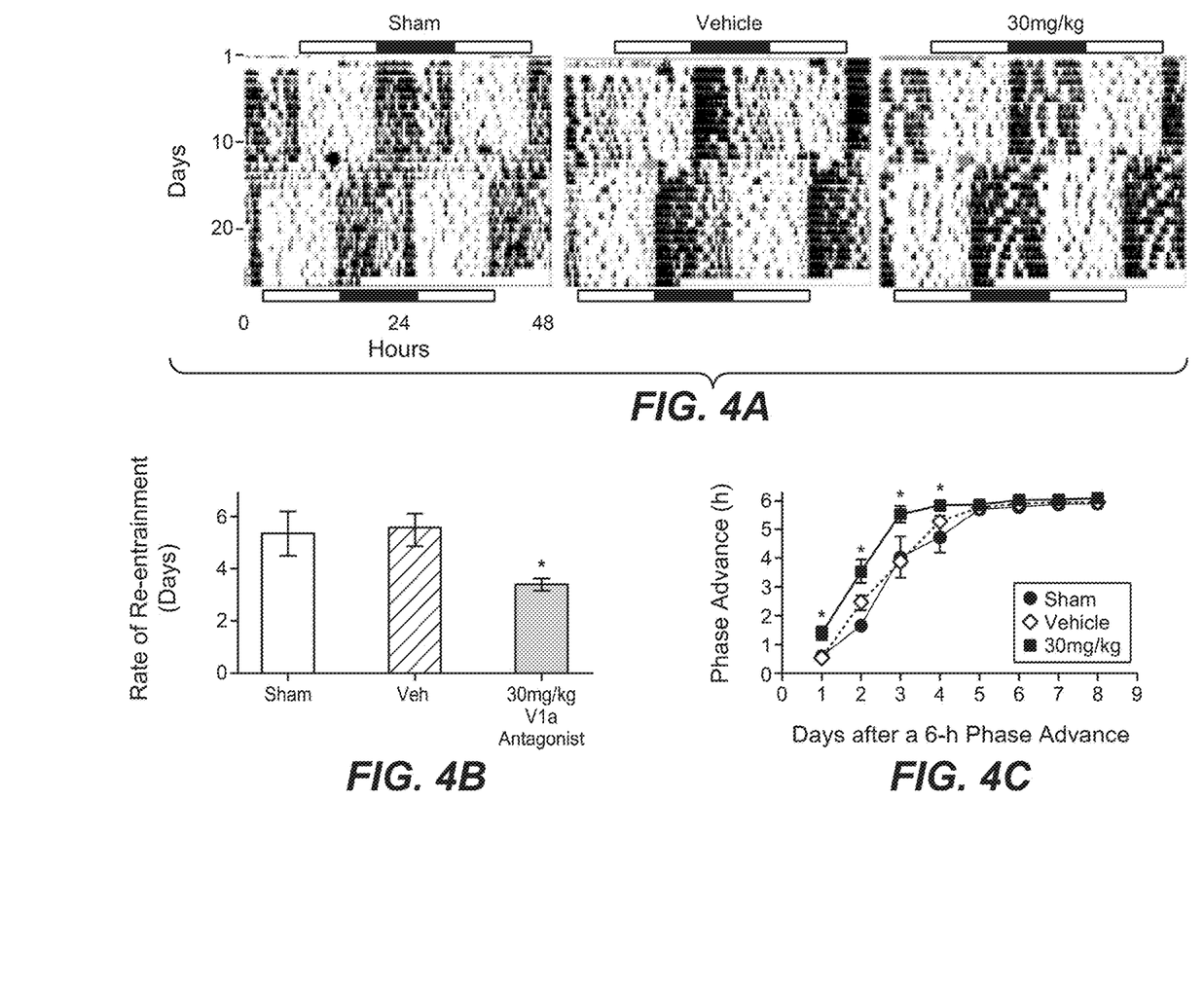

FIG. 4: (Top) Representative actograms of the locomotor activity of the different groups of naive mice treated at ZT/CT6 (mid rest period) and exposed to a 6 h phase advance shift of the LD cycle. Dots in actograms represent time of manipulation, and yellow and black bars in top and bottom indicate the light and dark period, respectively. (Middle) Rate of re-entrainment (number of days) to show full synchronization to the new LD cycle (sham n=3, vehicle n=4, 30 mg/kg n=5). The speed of entrainment was evaluated daily. From day 1 to 4 the 30 mg/kg group treated with the V1a antagonist trans-8-chloro-5-methyl-1-(4-pyridin-2-yloxycyclohexyl)-4,6-dihydro-[1,2,4]triazolo[4,3-a][1,4] benzodiazepine showed a significantly faster re-entrainment.

[1] Kalsbeek, A., E. Fliers, M. A. Hofman, D. F. Swaab and R. M. Buijs. 2010. Vasopressin and the output of the hypothalamic biological clock. 9999
[2] Schwartz, W. J., R. J. Coleman and S. M. Reppert. 1983. A daily vasopressin rhythm in rat cerebrospinal fluid. Brain Res 263: 105-12
[3] Groblewski, T. A., A. A. Nunez and R. M. Gold. 1981. Circadian rhythms in vasopressin deficient rats. Brain Res Bull 6: 125-30
[4] Albers, H. E., C. F. Ferris, S. E. Leeman and B. D. Goldman. 1984. Avian pancreatic polypeptide phase shifts hamster circadian rhythms when microinjected into the suprachiasmatic region. Science 223: 833-5
[5] Murphy, H. M., C. H. Wideman and G. R. Nadzam. 1998. The role of vasopressin in modulating circadian rhythm responses to phase shifts. Peptides 19: 1191-208
[6] Li, J. D., K. J. Burton, C. Zhang, S. B. Hu and Q. Y. Zhou. 2009. Vasopressin receptor V1a regulates circadian rhythms of locomotor activity and expression of clock-controlled genes in the suprachiasmatic nuclei. Am J Physiol Regul Integr Comp Physiol 296: R824-30
[7] Dubocovich, M. L., R. L. Hudson, I. C. Sumaya, M. I. Masana and E. Manna. 2005. Effect of MT1 melatonin receptor deletion on melatonin-mediated phase shift of circadian rhythms in the C57BL/6 mouse. Journal of Pineal Research 39: 113-120
[8] WO 2013/176220
[9] G L Patrick, *An Introduction to Medicinal Chemistry*, Second Edition, pages 239-250
[10] Ganellin and Roberts, *Medicinal Chemistry: The role of Organic Chemistry in Drug Research*, Second Edition, Academic Press Ltd (1993), Chapter 4
[11] Compendium of Chemical Terminology, 2nd, A. D. McNaught & A. Wilkinson (Eds). Blackwell Scientific Publications, Oxford (1997)

The invention claimed is:

1. A method for the treatment of phase shift sleep disorders, the method comprising administering to a subject in need thereof an effective amount of a compound of formula I wherein
$R^1$ is aryl or heteroaryl, unsubstituted or substituted with one or more substituents independently selected from A,
$R^2$ is H,
$C_{1-12}$-alkyl, unsubstituted or substituted with one or more OH, halo, cyano or $C_{1-12}$-alkoxy, —(CH$_2$)$_q$—R$^a$, wherein R$^a$ is phenyl or 5- or 6-membered heteroaryl, each unsubstituted or substituted with one or more substituents independently selected from A,
—(CH$_2$)$_r$NR$^i$R$^{ii}$,
—C(O)—C$_{1-12}$-alkyl, wherein C$_{1-12}$-alkyl is unsubstituted or substituted with one or more OH, halo, cyano or C$_{1-12}$-alkoxy,
—C(O)(CH$_2$)$_q$OC(O)—C$_{1-12}$-alkyl,
—C(O)(CH$_2$)$_q$NR$^i$ R$^{ii}$,
—C(O)O—C$_{1-12}$-alkyl, wherein alkyl is unsubstituted or substituted with one or more OH, halo, cyano or C$_{1-12}$-alkoxy,
—S(O)$_2$—C$_{1-12}$-alkyl, or
—S(O)$_2$NR$^i$ R$^{ii}$,
R$^i$ and R$^{ii}$ are each independently H, C$_{1-12}$-alkyl, or form together with the nitrogen to which they are bound a 3- to 7-membered heterocycloalkyl containing one or two heteroatoms selected from N, O or S, which heterocycloalkyl is unsubstituted or substituted by one or more substituents independently selected from B,
q is 1, 2, 3 or 4,
r is 2, 3 or 4,
A is halo, cyano, OH, C$_{1-7}$-alkyl, halo-C$_{1-7}$-alkyl, or C$_{1-7}$-alkoxy, halo-C$_{1-7}$-alkoxy, or hydroxy-C$_{1-7}$-alkyl,
B is oxo, halo, OH, C$_{1-7}$-alkyl or C$_{1-7}$-alkoxy,
R$^3$ is Cl or F,
or a pharmaceutically acceptable salt thereof.

2. The method of claim 1, wherein the phase shift sleep disorder is jetlag.

3. The method of claim 1, wherein
R$^1$ is a monovalent cyclic aromatic hydrocarbon moiety consisting of a mono- or bicyclic aromatic ring,
a monovalent 5- or 6-membered aromatic monocyclic or 9- or 10-membered aromatic bicyclic ring containing from one to four ring heteroatoms selected from N, O, or S, the remaining ring atoms being C, each unsubstituted or substituted with one or more substituents independently selected from A; and
A is is halo, cyano, OH, C$_{1-7}$-alkyl, halo-C$_{1-7}$-alkyl, C$_{1-7}$-alkoxy, halo-C$_{1-7}$alkoxy, hydroxy-C$_{1-7}$-alkyl.

4. The method of claim 1, wherein R$^1$ is a monovalent cyclic aromatic hydrocarbon moiety consisting of a monoaromatic ring.

5. The method of claim 1, wherein R$^1$ is pyridinyl.

6. The method of claim 1, wherein R$^2$ is
H,
C$_{1-12}$-alkyl, unsubstituted or substituted with one or more OH,
—(CH$_2$)$_q$—R$^a$, wherein R$^a$ is phenyl or 5- or 6-membered heteroaryl and q is 1, 2, 3 or 4,
—C(O)—C$_{1-12}$-alkyl,
—C(O)(CH$_2$)$_q$NR$^i$R$^{ii}$, wherein R$^i$ and R$^{ii}$ are each independently H or C$_{1-12}$-alkyl, and q is 1, 2, 3 or 4,
—C(O)O—C$_{1-12}$-alkyl,
—S(O)$_2$—C$_{1-12}$-alkyl, or
—S(O)$_2$NR$^i$R$^{ii}$, wherein R$^i$ and R$^{ii}$ are each independently H or C$_{1-12}$-alkyl.

7. The method of claim 1, wherein R$^2$ is methyl.

8. The method of claim 1, wherein R$^3$ is Cl.

9. The method of claim 1, wherein the compound is selected from the group consisting of
trans-8-Chloro-1-(4-phenoxy-cyclohexyl)-4H,6H-2,3,5,10b-tetraaza-benzoazulene-5-carboxylic acid tert-butyl ester,
trans-8-Chloro-1-(4-phenoxy-cyclohexyl)-5,6-dihydro-4H-2,3,5,10b-tetraaza-benzoazulene hydrochloride,
trans-8-Chloro-5-methyl-1-(4-phenoxy-cyclohexyl)-5,6-dihydro-4H-2,3,5,10b-tetraaza-benzo[e]azulene,
trans-1-[8-Chloro-1-(4-phenoxy-cyclohexyl)-4H,6H-2,3,5,10b-tetraaza-benzoazulen-5-yl]-ethanone,
trans-8-Chloro-5-methanesulfonyl-1-(4-phenoxy-cyclohexyl)-5,6-dihydro-4H-2,3,5,10b-tetraaza-benzoazulene,
trans-2-[8-Chloro-1-(4-phenoxy-cyclohexyl)-4H,6H-2,3,5,10b-tetraaza-benzoazulen-5-yl]-ethanol,
trans-8-Chloro-5-isopropyl-1-(4-phenoxy-cyclohexyl)-5,6-dihydro-4H-2,3 ,5,10b-tetraaza-benzoazulene,
trans-8-Chloro-1-(4-phenoxy-cyclohexyl)-4H,6H-2,3,5,10b-tetraaza-benzoazulene-5-sulfonic acid dimethylamide,
trans-8-Chloro-1-(4-phenoxy-cyclohexyl)-5-pyridin-2-ylmethyl-5,6-dihydro-4H-2,3,5,10b-tetraaza-benzoazulene,
trans-1-[8-Chloro-1-(4-phenoxy-cyclohexyl)-4H,6H-2,3,5,10b-tetraaza-benzoazulen-5-yl]-2-dimethylamino-ethanone,
trans-8-Fluoro-1-(4-phenoxy-cyclohexyl)-4H,6H-2,3,5,10b-tetraaza-benzo[e]azulene-5-carboxylic acid tert-butyl ester,
trans-8-Fluoro-5-methyl-1-(4-phenoxy-cyclohexyl)-5,6-dihydro-4H-2,3,5,10b-tetraaza-benzoazulene,
cis-8-Chloro-1-(4-phenoxy-cyclohexyl)-4H,6H-2,3,5,10b-tetraaza-benzoazulene-5-carboxylic acid tert-butyl ester,
cis-8-Chloro-5-methyl-1-(4-phenoxy-cyclohexyl)-5,6-dihydro-4H-2,3,5,10b-tetraaza-benzoazulene,
trans-8-Chloro-1-[4-(4-fluoro-phenoxy)-cyclohexyl]-4H,6H-2,3,5,10b-tetraaza-benzoazulene-5-carboxylic acid tert-butyl ester,
trans-8-Chloro-1-[4-(4-fluoro-phenoxy)-cyclohexyl]-5,6-dihydro-4H-2,3,5,10b-tetraaza-benzo[e]azulene hydrochloride,
trans-8-Chloro-1-[4-(4-fluoro-phenoxy)-cyclohexyl]-5-methyl-5,6-dihydro-4H-2,3,5,10b-tetraaza-benzoazulene,
trans-8-Chloro-1-[4-(4-cyano-phenoxy)-cyclohexyl]-4H,6H-2,3,5,10b-tetraaza-benzo[e]azulene-5-carboxylic acid tert-butyl ester,
trans-4-[4-(8-Chloro-5-methyl-5,6-dihydro-4H-2,3,5,10b-tetraaza-benzo[e]azulen-1-yl)-cyclohexyloxy]-benzonitrile,
trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester,
trans-8-Chloro-1-[4-(3-chloro-phenoxy)-cyclohexyl]-4H,6H-2,3,5,10b-tetraaza-benzoazulene-5-carboxylic acid tert-butyl ester,
trans-8-Chloro-1-[4-(3-chloro-phenoxy)-cyclohexyl]-5-methyl-5,6-dihydro-4H-2,3,5,10b-tetraaza-benzoazulene,
trans-8-Chloro-1-[4-(3-methoxy-phenoxy)-cyclohexyl]-4H,6H-2,3,5,10b-tetraaza-benzoazulene-5-carboxylic acid tert-butyl ester,
trans-8-Chloro-1-[4-(3-methoxy-phenoxy)-cyclohexyl]-5,6-dihydro-4H-2,3,5,10b-tetraaza-benzo[e]azulene hydrochloride,
trans-8-Chloro-1-[4-(3-methoxy-phenoxy)-cyclohexyl]-5-methyl-5,6-dihydro-4H-2,3,5,10b-tetraaza-benzoazulene,
trans-3-[4-(8-Chloro-5-methyl-5,6-dihydro-4H-2,3,5,10b-tetraaza-benzoazulen-1-yl)-cyclohexyloxy]-benzonitrile,
trans-8-Chloro-1-(4-m-tolyloxy-cyclohexyl)-4H,6H-2,3,5,10b-tetraaza-benzo [e]azulene-5-carboxylic acid tert-butyl ester,
trans-8-Chloro-1-(4-m-tolyloxy-cyclohexyl)-5,6-dihydro-4H-2,3,5,10b-tetraaza-benzo[e]azulene hydrochloride, trans-8-Chloro-5-methyl-1-(4-m-tolyloxy-cyclohexyl)-5,6-dihydro-4H-2,3,5,10b-tetraaza-benzo[e]azulene, trans-1-[4-(3-tert-Butyl-phenoxy)-cyclohexyl]-8-chloro-4H,6H-2,3,5,10b-tetraaza-benzo[e]azulene-5-carboxylic acid tert-butyl ester, trans-8-Chloro-1-[4-(2-fluoro-phenoxy)-cyclohexyl]-4H,6H-2,3,5,10b-tetraaza-benzo[e]azulene-5-carboxylic acid tert-butyl ester, trans-8-Chloro-1-[4-(2-fluoro-phenoxy)-cyclohexyl]-5,6-dihydro-4H-2,3,5,10b-tetraaza-benzo[e]azulene hydrochloride, trans-8-Chloro-1-[4-(2-fluoro-phenoxy)-cyclohexyl]-5-methyl-5,6-dihydro-4H-2,3,5,10b-tetraaza-benzo[e]azulene, trans-8-Chloro-1-[4-(2-cyano-phenoxy)-cyclohexyl]-4H,6H-2,3,5,10b-tetraaza-benzoazulene-5-carboxylic acid tert-butyl ester, trans-2-[4-(8-Chloro-5,6-dihydro-4H-2,3,5,10b-tetraaza-benzo[e]azulen-1-yl)-cyclohexyloxy]-benzonitrile hydrochloride, trans-2-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-o-tolyloxy-cyclohexyl)-4H,6H-2,3,5,10b-tetraaza-benzoazulene-5-carboxylic acid tert-butyl ester, trans-8-Chloro-5-methyl-1-(4-o-tolyloxy-cyclohexyl)-5,6-dihydro-4H-2,3,5,10b-tetraaza-benzoazulene, trans-8-Chloro-1-[4-(3,5-difluoro-phenoxy)-cyclohexyl]-4H,6H-2,3,5,10b-tetraaza-benzoazulene-5-carboxylic acid tert-butyl ester, trans-8-Chloro-1-[4-(3,5-difluoro-phenoxy)-cyclohexyl]-5-methyl-5,6-dihydro-4H-2,3,5,10b-tetraaza-benzoazulene, trans-8-Chloro-1-[4-(naphthalen-2-yloxy)-cyclohexyl]-4H,6H-2,3,5,10b-tetraaza-benzoazulene-5-carboxylic acid tert-butyl ester, trans-8-Chloro-5-methyl-1-[4-(naphthalen-2-yloxy)-cyclohexyl]-5,6-dihydro-4H-2,3,5,10b-tetraaza-benzoazulene, trans-8-Chloro-1-[4-(pyridin-3-yloxy)-cyclohexyl]-4H,6H-2,3,5,10b-tetraaza-benzoazulene-5-carboxylic acid tert-butyl ester, trans-8-Chloro-5-methyl-1-[4-(pyridin-3-yloxy)-cyclohexyl]-5,6-dihydro-4H-2,3,5,10b-tetraaza-benzoazulene, trans-8-Chloro-1-[4-(5-chloro-pyridin-3-yloxy)-cyclohexyl]-4H,6H-2,3,5,10b-tetraaza-benzoazulene-5-carboxylic acid tert-butyl ester, trans-8-Chloro-1-[4-(5-chloro-pyridin-3-yloxy)-cyclohexyl]-5-methyl-5,6-dihydro-4H-2,3,5,10b-tetraaza-benzoazulene, trans-8-Chloro-1-[4-(pyridin-2-yloxy)-cyclohexyl]-4H,6H-2,3,5,10b-tetraaza-benzoazulene-5-carboxylic acid tert-butyl ester, trans-8-Chloro-1-[4-(pyridin-2-yloxy)-cyclohexyl]-5,6-dihydro-4H-2,3,5,10b-tetraaza-benzoazulene hydrochloride, trans-8-Chloro-(5-methyl-1-[4-(pyridin-2-yloxy)-cyclohexyl]-5,6-dihydro-4H-2,3,5,10b-tetraaza-benzoazulene, trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester, trans-8-Chloro-1-[4-(6-chloro-pyridin-2-yloxy)-cyclohexyl]-5-methyl-5,6-dihydro-4H-2,3,5,10b-tetraaza-benzo[e]azulene, trans-8-Chloro-1-[4-(5-chloro-pyridin-2-yloxy)-cyclohexyl]-5,6-dihydro-4H-2,3,5,10b-tetraaza-benzo[e]azulene hydrochloride, trans-8-Chloro-1-[4-(5-chloro-pyridin-2-yloxy)-cyclohexyl]-5-methyl-5,6-dihydro-4H-2,3,5,10b-tetraaza-benzo[e]azulene, trans-8-Chloro-1-[4-(pyrimidin-2-yloxy)-cyclohexyl]-4H,6H-2,3,5,10b-tetraaza-benzo[e]azulene-5-carboxylic acid tert-butyl ester, cis-8-Chloro-1-[4-(pyrimidin-2-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrimidin-2-yloxy)-cyclohexyl]-5,6-dihydro-4H-2,3,5,10b-tetraaza-benzo[e]azulene, trans-8-Chloro-1-[4-(pyrazin-2-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrazin-2-yloxy)-cyclohexyl]-5,6-dihydro-4H-2,3,5,10b-tetraaza-benzo[e]azulene, trans-8-Chloro-1-[4-(pyrimidin-4-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrimidin-4-yloxy)-cyclohexyl]-5,6-dihydro-4H-2,3,5,10b-tetraaza-benzo[e]azulene, trans-8-Chloro-1-[4-(pyridazin-3-yloxy)-cyclohexyl]-4H,6H-2,3,5,10b-tetraaza-benzo[e]azulene-5-carboxylic acid tert-butyl ester, cis-8-Chloro-1-[4-(pyridazin-3-yloxy)-cyclohexyl]-4H,6H-2,3,5,10b-tetraaza-benzo[e]azulene-5-carboxylic acid tert-butyl ester, trans-8-Chloro-5-methyl-1-[4-(pyridazin-3-yloxy)-cyclohexyl]-5,6-dihydro-4H-2,3,5,10b-tetraaza-benzo[e]azulene, cis-8-Chloro-1-[4-(pyridin-2-yloxy)-cyclohexyl]-4H,6H-2,3,5 10b-tetraaza-benzo[e]azulene-5-carboxylic acid tert-butyl ester , cis-8-Chloro-1-[4-(pyridin-2-yloxy)-cyclohexyl]-5,6-dihydro-4H-2,3,5,10b-tetraaza-benzo[e]azulene, cis-8-Chloro-5-methyl-1-[4-(pyridin-2-yloxy)-cyclohexyl]-5,6-dihydro-4H-2,3,5,10b-tetraaza-benzo[e]azulene, trans-8-Chloro-1-[4-(3-fluoro-pyridin-2-yloxy)-cyclohexyl]-5,6-dihydro-4H-2,3,5,10b-tetraaza-benzo[e]azulene, trans-8-Chloro-1-[4-(3-fluoro-pyridin-2-yloxy)-cyclohexyl]-5-methyl-5,6-dihydro-4H-2,3,5,10b-tetraaza-benzo[e]azulene, trans-8-Chloro-1-[4-(5-fluoro-pyridin-2-yloxy)-cyclohexyl]-5,6-dihydro-4H-2,3,5,10b-tetraaza-benzo[e]azulene trans-8-Chloro-1-[4-(5-fluoro-pyridin-2-yloxy)-cyclohexyl]-5-methyl-5,6-dihydro-4H-2,3,5,10b-tetraaza-benzo[e]azulene, trans-8-Chloro-1-[4-(6-methyl-pyridin-2-yloxy)-cyclohexyl]-5,6-dihydro-4H-2,3,5,10b-tetraaza-benzo[e]azulene, trans-8-Chloro-5-(2,2-difluoro-ethyl)-1-[4-(6-methyl-pyridin-2-yloxy)-cyclohexyl]-5,6-dihydro-4H-2,3,5,10b-tetraaza-benzo[e]azulene, trans-8-Chloro-5-(2-fluoro-ethyl)-1-[4-(5-fluoro-pyridin-2-yloxy)-cyclohexyl]-5,6-dihydro-4H-2,3,5,10b-tetraaza-benzo[e]azulene, trans-8-Chloro-5-ethyl-1-[4-(3-fluoro-pyridin-2-yloxy)-cyclohexyl]-5,6-dihydro-4H-2,3,5,10b-tetraaza-benzo[e]azulene, trans-8-Chloro-5-ethyl-1-[4-(5-fluoro-pyridin-2-yloxy)-cyclohexyl]-5,6-dihydro-4H-2,3,5,10b-tetraaza-benzo[e]azulene, trans-8-Chloro-5-ethyl-1-[4-(6-methyl-pyridin-2-yloxy)-cyclohexyl]-5,6-dihydro-4H-2,3,5,10b-tetraaza-benzo[e]azulene

[e]azulene, and trans-8-Chloro-5-methyl-1-[4-(6-methyl-pyridin-2-yloxy)-cyclohexyl]-5,6-dihydro-4H-2,3,5,10b-tetraaza-benzo[e]azulene;
or a pharmaceuticaly acceptable salt thereof.

10. The method of claim 1, wherein the V1a antagonist is or a pharmaceuticaly acceptable salt thereof.

11. The method of claim 6, wherein $R^2$ is
H,
$C_{1-12}$-alkyl, unsubstituted or substituted with one or more OH,
—$(CH_2)_q$-$R^a$, wherein $R^a$ is phenyl or 5- or 6-membered heteroaryl and q is 1,
—$C(O)$—$C_{1-12}$-alkyl,
—$C(O)(CH_2)_q NR^i R^{ii}$, wherein $R^i$ and $R^{ii}$ are each $C_{1-12}$-alkyl, and q is 1,
—$C(O)O$—$C_{1-12}$-alkyl,
—$S(O)_2$—$C_{1-12}$-alkyl, or
—$S(O)_2 NR^i R^{ii}$, wherein $R^i$ and $R^{ii}$ are $C_{1-12}$-alkyl.

* * * * *